(12) United States Patent
Vijayachandran

(10) Patent No.: US 11,980,393 B2
(45) Date of Patent: May 14, 2024

(54) TWO-PIECE SEPARABLE OBTURATOR

(71) Applicant: Cilag GmbH International, Zug (CH)

(72) Inventor: Sajayesh Vijayachandran, Kannur (IN)

(73) Assignee: Cilag GmbH International, Zug (CH)

( * ) Notice: Subject to any disclaimer, the term of this patent is extended or adjusted under 35 U.S.C. 154(b) by 335 days.

(21) Appl. No.: 17/213,431

(22) Filed: Mar. 26, 2021

(65) Prior Publication Data

US 2021/0338275 A1 Nov. 4, 2021

(30) Foreign Application Priority Data

May 1, 2020 (IN) .............................. 202011018667

(51) Int. Cl.
*A61B 17/34* (2006.01)
*A61B 17/00* (2006.01)

(52) U.S. Cl.
CPC .. *A61B 17/3423* (2013.01); *A61B 2017/0023* (2013.01); *A61B 2017/00477* (2013.01); *A61B 2017/3454* (2013.01)

(58) Field of Classification Search
CPC ........ A61B 17/3423; A61B 2017/0023; A61B 2017/00477; A61B 2017/3454
See application file for complete search history.

(56) References Cited

U.S. PATENT DOCUMENTS 4,699,616 A 10/1987 Nowak et al.
5,147,316 A 9/1992 Castillenti
5,215,531 A 6/1993 Maxson et al.
5,256,147 A * 10/1993 Vidal ................. A61B 17/3417
604/274

(Continued)

FOREIGN PATENT DOCUMENTS

AU 702882 B2 3/1993
CN 106344126 B 2/2019
(Continued)

OTHER PUBLICATIONS

International Search Report and Written Opinion dated Jul. 22, 2021, for International Application No. PCT/EP2021/061421, 15 pages.

(Continued)

*Primary Examiner* — Nicholas J Plionis
(74) *Attorney, Agent, or Firm* — Frost Brown Todd LLP

(57) ABSTRACT

A surgical access device includes an obturator head, an elongated shaft extending distally from the obturator head along a longitudinal axis, and an obturator tip. The obturator tip includes a reusable portion and a replaceable tip. The reusable portion is attached to a distal portion of the elongated shaft such that the reusable portion is configured to be sterilized with the elongated shaft. The replaceable tip includes a tapered distal tip and a proximal coupling body. The tapered distal tip is configured to facilitate insertion of the surgical access device through a body wall of the patient. The proximal coupling body is configured to selectively couple with the reusable portion. The replaceable tip, in its entirety, is movable relative to the reusable portion along a mating path in order to couple the proximal coupling body with the reusable portion. The mating path extends laterally relative to the longitudinal axis.

19 Claims, 14 Drawing Sheets

(56) References Cited

U.S. PATENT DOCUMENTS

| | | | |
|---|---|---|---|
| 5,263,939 A | 11/1993 | Wortrich | |
| 5,267,970 A | 12/1993 | Chin et al. | |
| 5,364,372 A | 11/1994 | Danks et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 6,638,265 B1 | 10/2003 | Ternamian | |
| 7,981,092 B2 | 7/2011 | Duke | |
| 8,226,553 B2 | 7/2012 | Shelton, IV et al. | |
| 8,251,900 B2 | 8/2012 | Ortiz et al. | |
| 8,479,969 B2 | 7/2013 | Shelton, IV | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 10,327,809 B2 | 6/2019 | Buyda et al. | |
| 10,792,069 B2 | 10/2020 | Hall et al. | |
| 10,820,924 B2 | 11/2020 | Hall et al. | |
| 2005/0267419 A1* | 12/2005 | Smith | A61B 17/0218 604/256 |
| 2009/0182282 A1 | 7/2009 | Okihisa et al. | |
| 2010/0010449 A1 | 1/2010 | Leibowitz et al. | |
| 2011/0295269 A1* | 12/2011 | Swensgard | A61B 34/76 606/130 |
| 2013/0060084 A1 | 3/2013 | Fouts et al. | |
| 2014/0066953 A1 | 3/2014 | Keating et al. | |
| 2016/0015423 A1 | 1/2016 | Ravikumar et al. | |
| 2018/0021061 A1* | 1/2018 | Reid | A61B 17/3423 600/210 |
| 2018/0199959 A1 | 7/2018 | Lee | |
| 2018/0206883 A1 | 7/2018 | McIntyre et al. | |
| 2019/0000496 A1 | 1/2019 | Shelton, IV et al. | |
| 2019/0380742 A1 | 12/2019 | Hall et al. | |
| 2021/0338269 A1 | 11/2021 | Scott et al. | |
| 2021/0338272 A1 | 11/2021 | Muthuchidambaram et al. | |
| 2021/0338273 A1 | 11/2021 | Vijayachandran et al. | |
| 2021/0338274 A1 | 11/2021 | Scott et al. | |
| 2021/0338276 A1 | 11/2021 | Scott | |
| 2021/0338278 A1 | 11/2021 | Scott et al. | |
| 2021/0338281 A1 | 11/2021 | Mozloom, Jr. et al. | |
| 2021/0338282 A1 | 11/2021 | Vijayachandran | |
| 2021/0338283 A1 | 11/2021 | McLain | |
| 2021/0338371 A1 | 11/2021 | Harris et al. | |

FOREIGN PATENT DOCUMENTS

| | | |
|---|---|---|
| DE | 202007001745 U2 | 4/2007 |
| EP | 2174602 A1 | 4/2010 |
| WO | WO 1999/052457 A1 | 10/1999 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

* cited by examiner

TWO-PIECE SEPARABLE OBTURATOR

PRIORITY

This Application claims priority to Indian Provisional Pat. App. No. 2020/11018667, entitled "Two-Piece Separable Obturator," filed on May 1, 2020.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
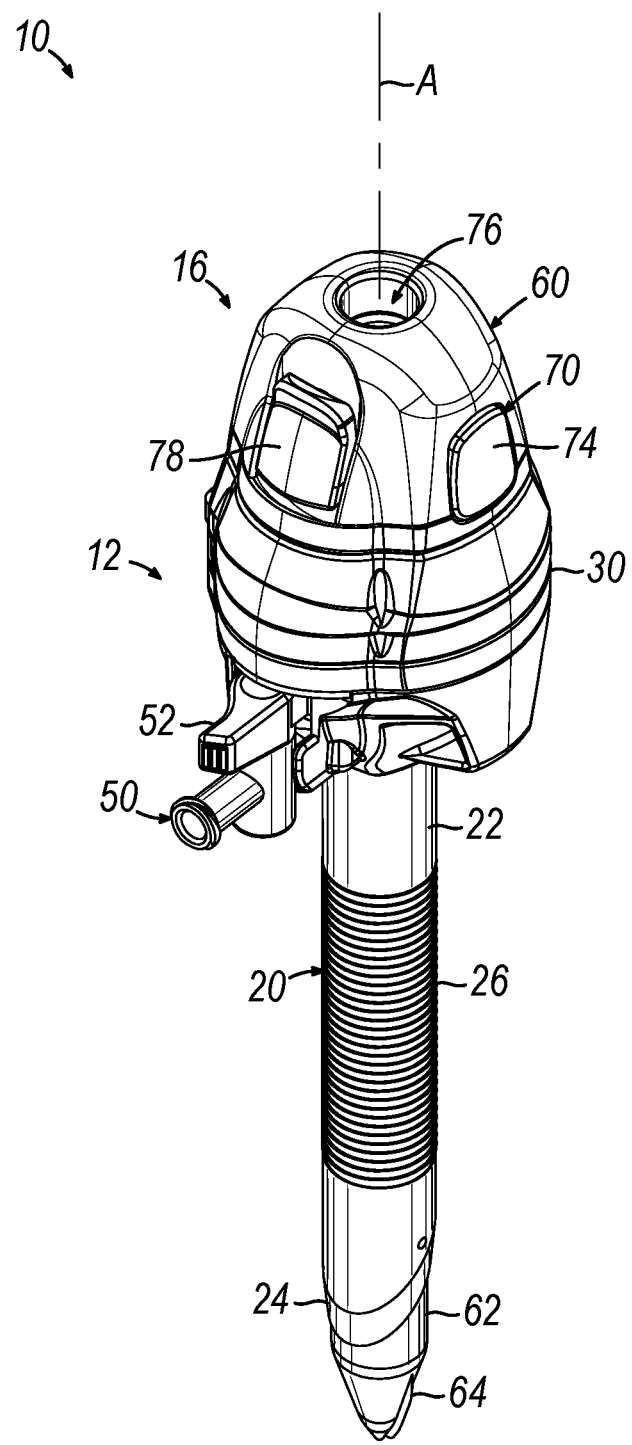
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
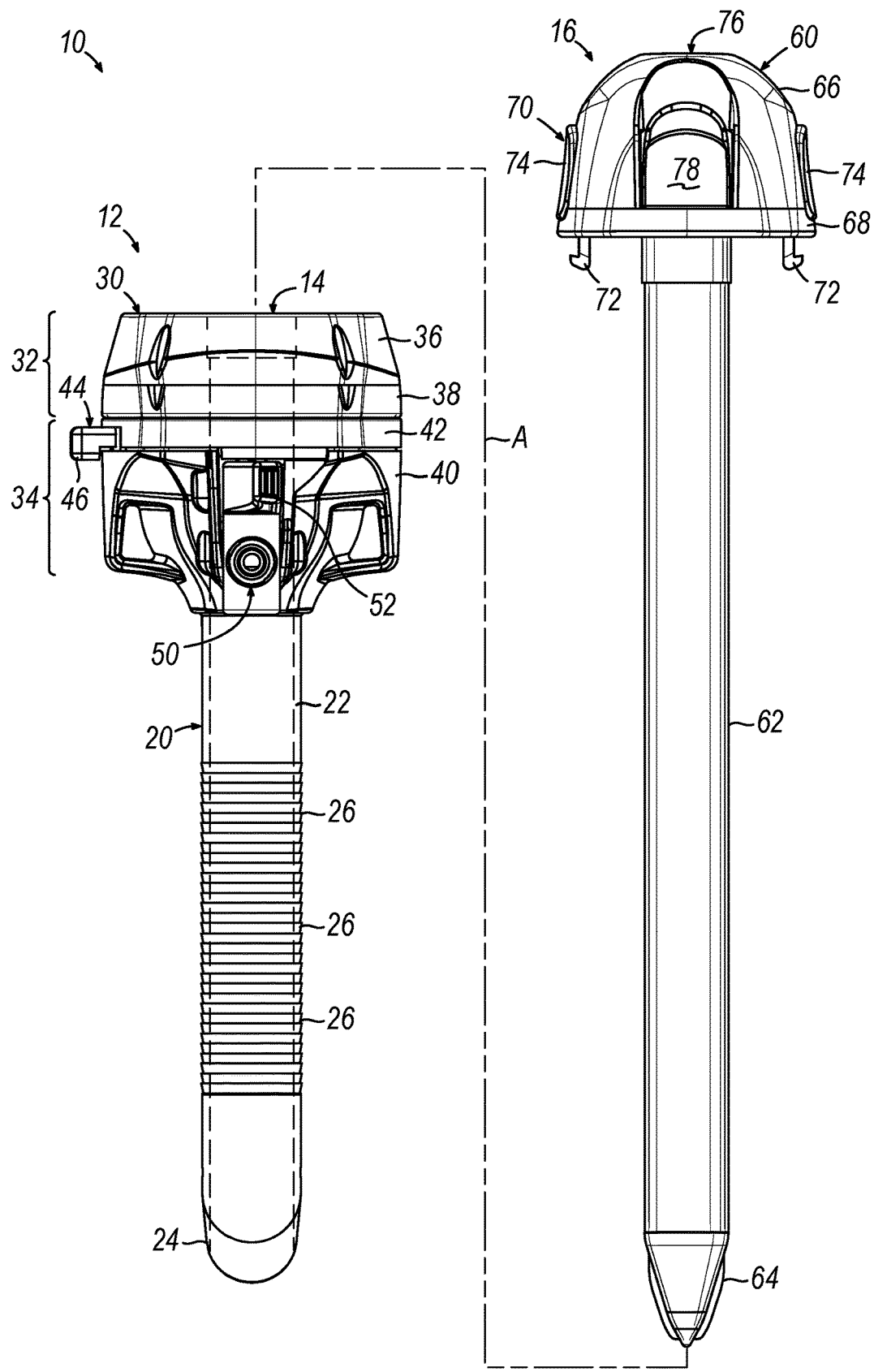
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
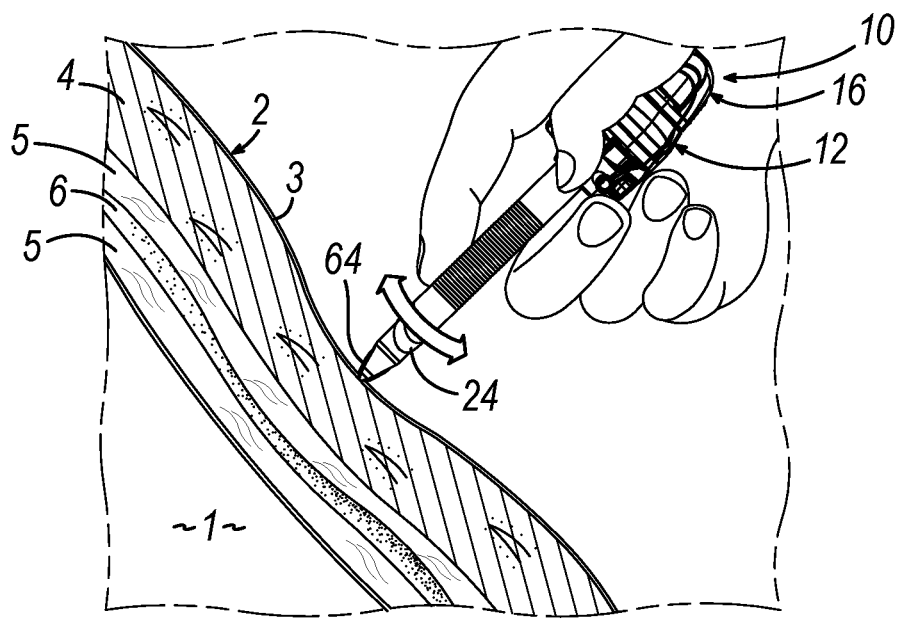
FIG. 3A depicts a side sectional view of the trocar of FIG. 1 being manipulated by a clinician through tissue layers of an abdominal wall.
Figure 3B:
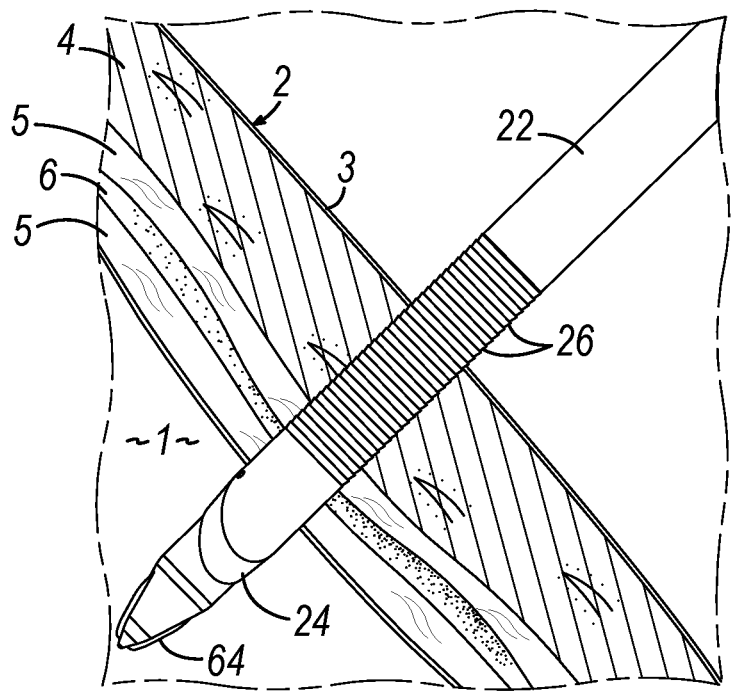
FIG. 3B depicts an enlarged side sectional view of the trocar of FIG. 1, showing a distal end of the trocar received within the abdominal cavity of FIG. 3A.
Figure 3C:
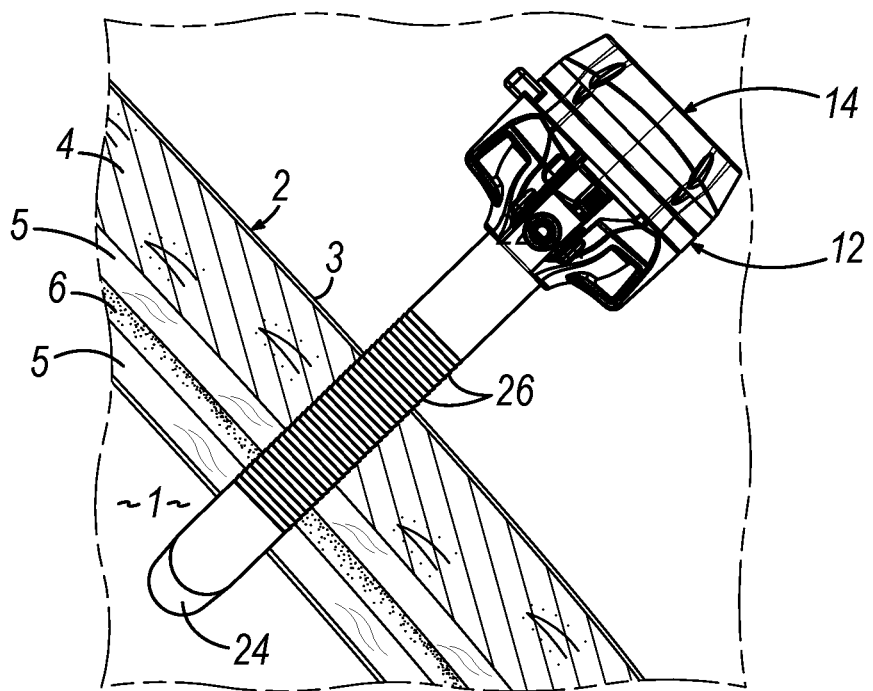
FIG. 3C depicts a side sectional view of the cannula assembly of FIG. 1, showing the cannula assembly remaining positioned within the abdominal wall of FIG. 3A following detachment and removal of the obturator.
Figure 3D:
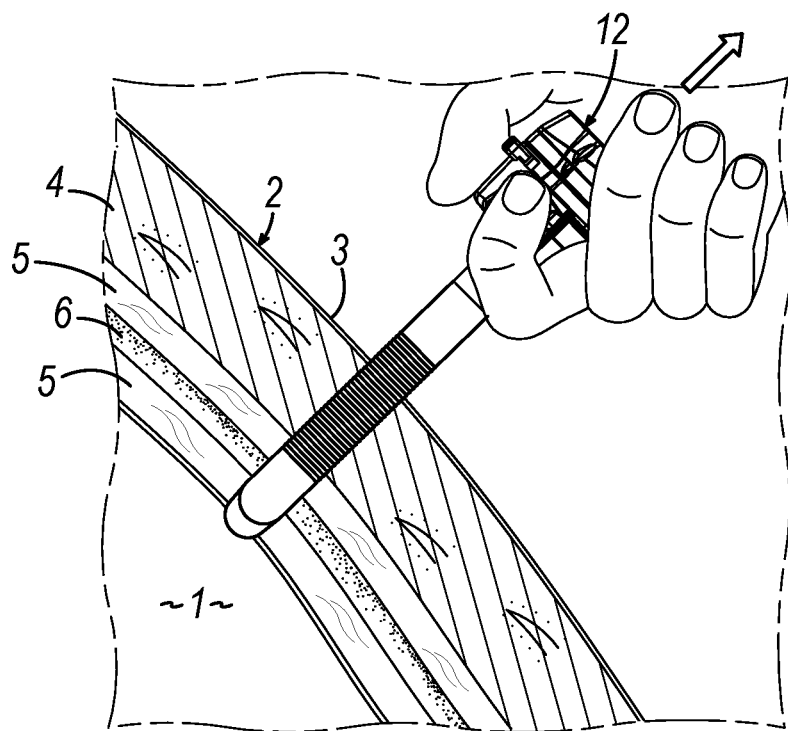
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
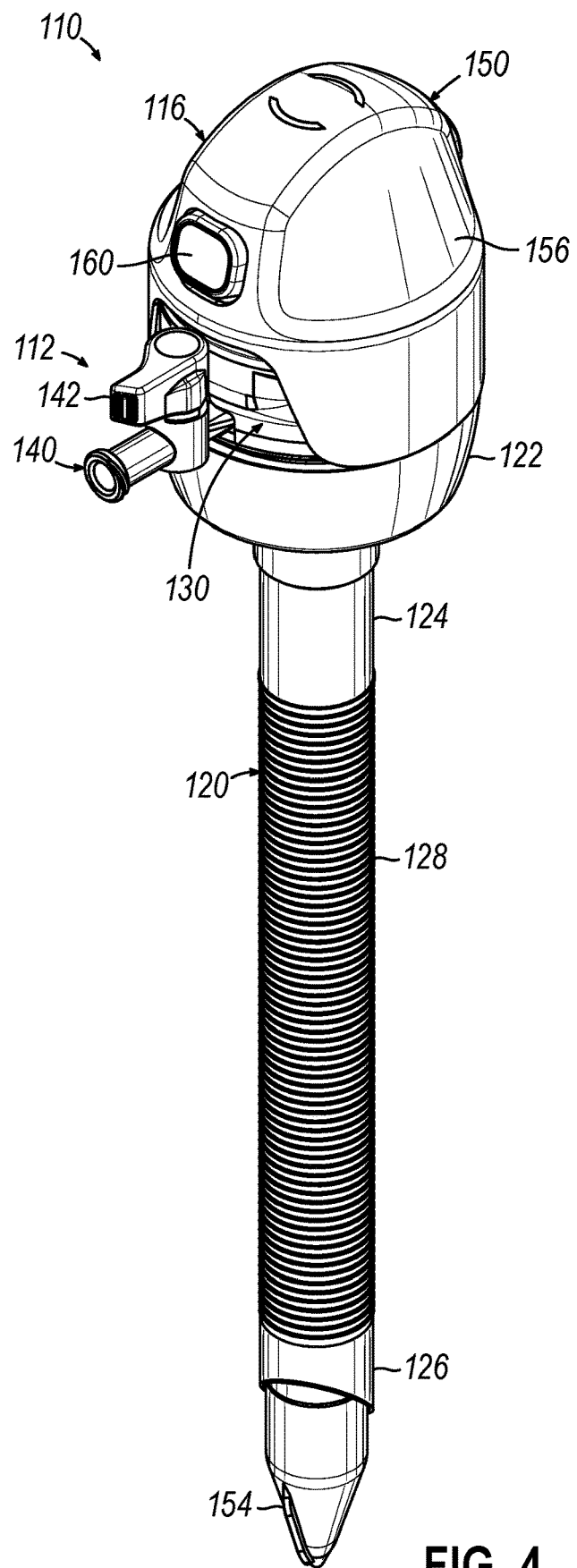
FIG. 4 depicts a perspective view of another exemplary trocar having a cannula assembly and an obturator shown in an assembled state.
Figure 5:
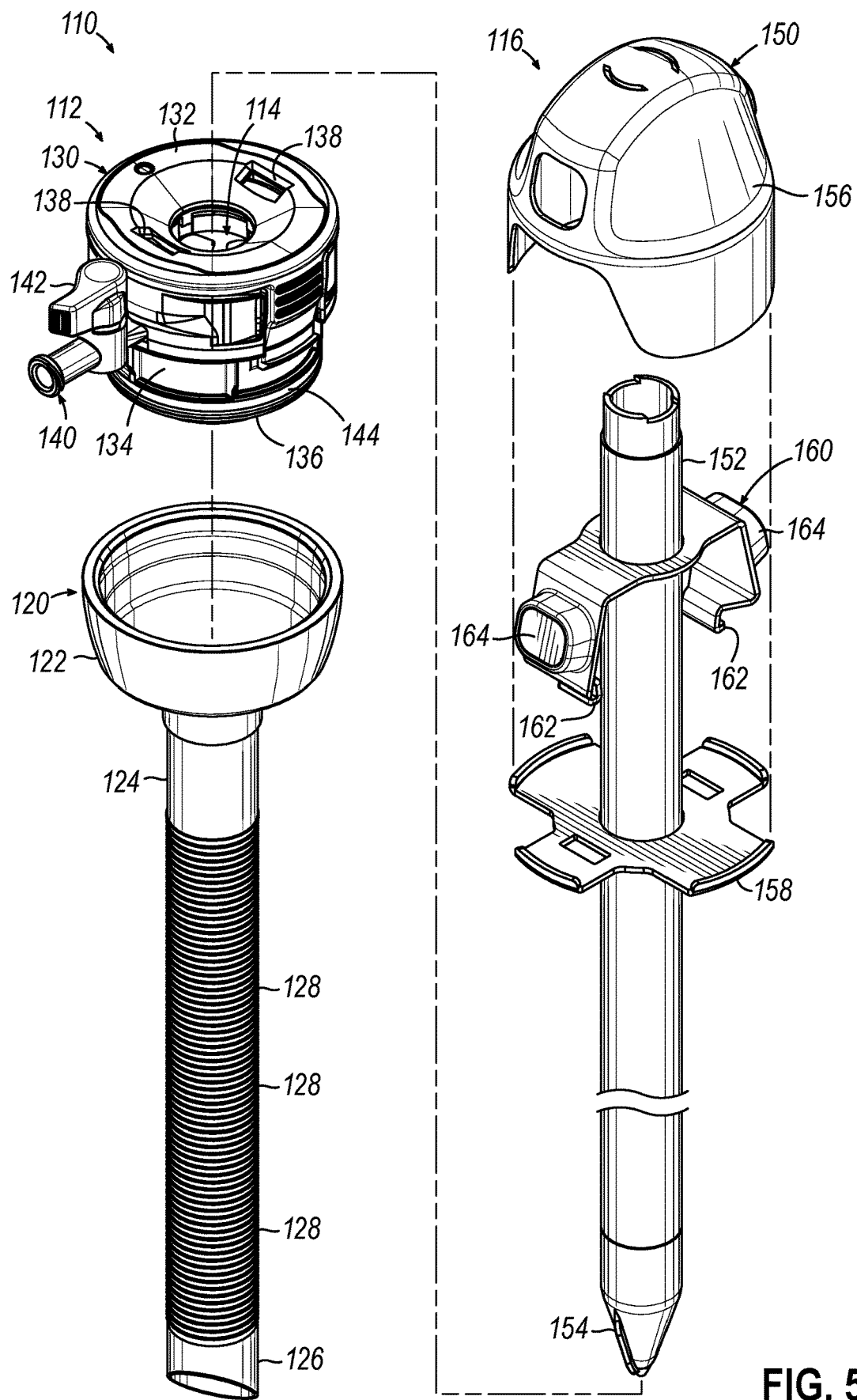
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Obturators Having Multiple Components

As mentioned above, while obturator (16, 116) is suitably received within cannula assembly (12, 112), obturator tip (64, 154) is configured to urge against skin (3) inward through the various layers forming the patient's abdominal wall (2) such that obturator tip (64, 154) and cannula tip (24, 126) suitably access the abdominal cavity (1). In some instances, obturator tip (64, 154) may comprise a "bladeless tip" obturator. A "bladeless tip" obturator includes a tip geometry that is sharp enough, yet not too sharp, in order to allow for atraumatic, yet easy-to-use, tissue spreading of the patient's abdominal wall (2) during trocar (10, 110) entry in accordance with the description above.

As also mentioned above, in some instances, it may be desirable to configure a trocar such that one or more components thereof may be sterilized and reused for multiple surgical procedures, while one or more other components may be (A) easily and economically disposed of and replaced after each procedure, and/or (B) sterilized and reused for a second, smaller number of procedures. Therefore, cannula (12, 120) and obturator (16, 116) may be constructed of a robust material, such as surgical steel, such that they may be sterilized and reused for multiple surgical procedures.

However, in instances where obturator (16, 116) is configured to be sterilized and reused, the tip geometry of obturator tip (64, 154) may eventually deviate from intended dimensions through wear, degradation, damage, etc., after numerous uses in accordance with the description herein. Deviation of tip geometry of obturator tip (64, 154) may be undesirable, as obturator tip (64, 154) may no longer be sharp enough for trocar (10, 110) to suitably access the abdominal cavity (1) via atraumatic, yet easy-to-use, tissue spreading in accordance with the teachings herein. Therefore, it may be desirable to have an obturator that includes a replaceable obturator tip configured to eventually be disposed of and replaced, while other portions of the obturator may be sterilized and reused multiple times after.

Figure 6A:
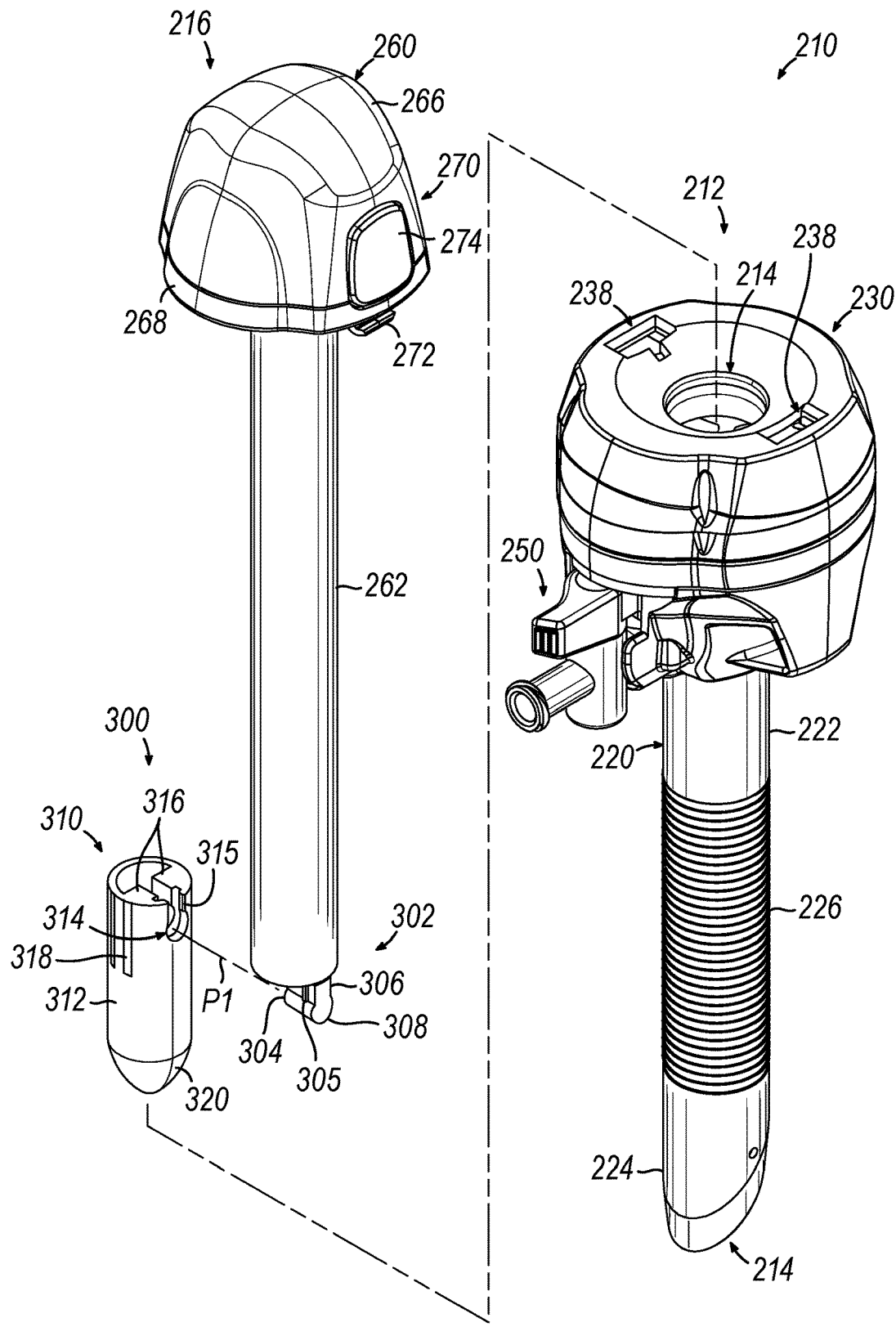
FIG. 6A depicts a perspective view of another exemplary trocar having a cannula assembly and an obturator assembly shown in a disassembled state, the obturator assembly having a replaceable tip assembly shown in a disassembled state.
Figure 6B:
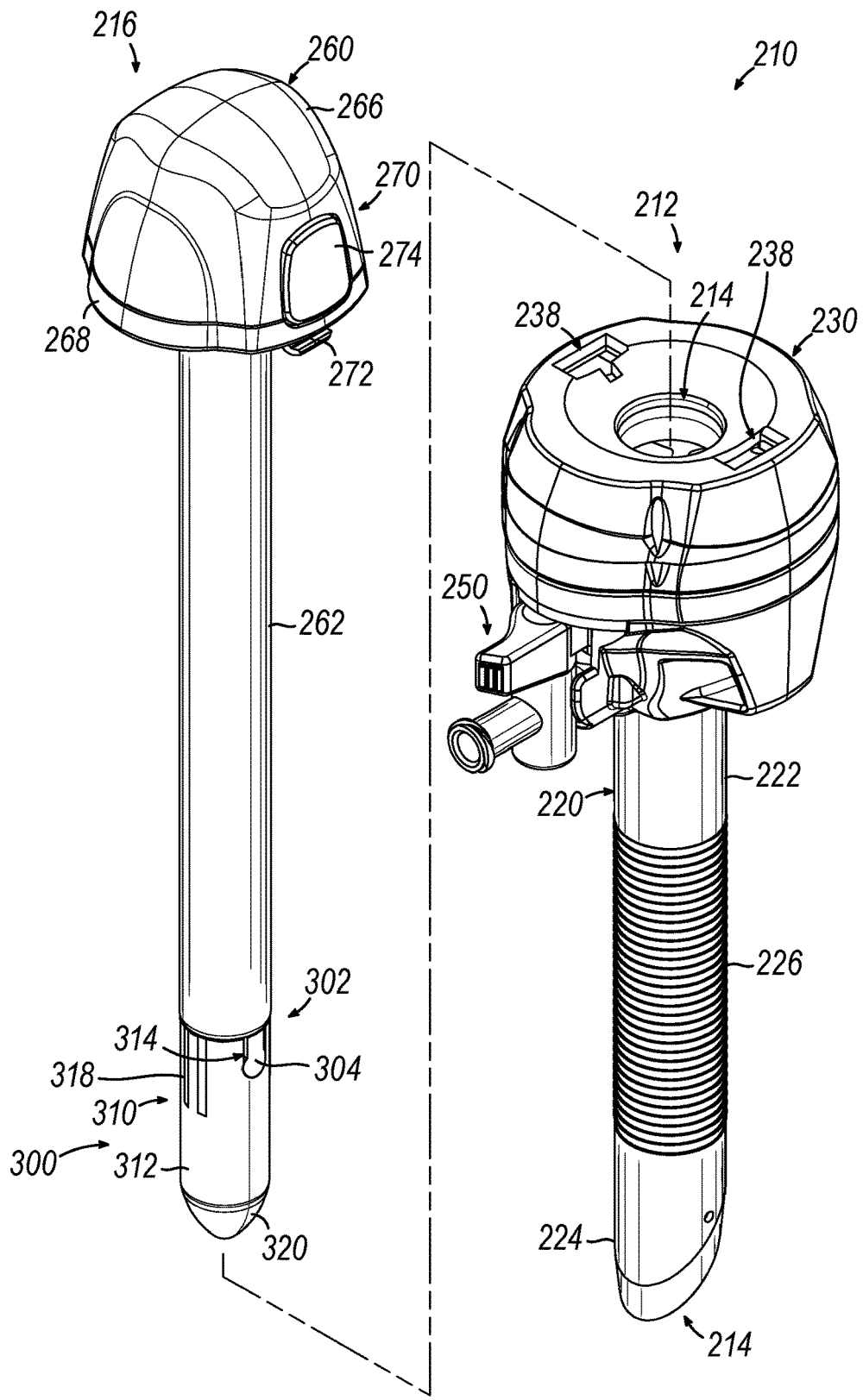
FIG. 6B depicts a perspective view of the trocar of FIG. 6A, where the cannula assembly and the obturator assembly are in the disassembled state, where the replaceable tip assembly is in an assembled state.
Figure 6C:
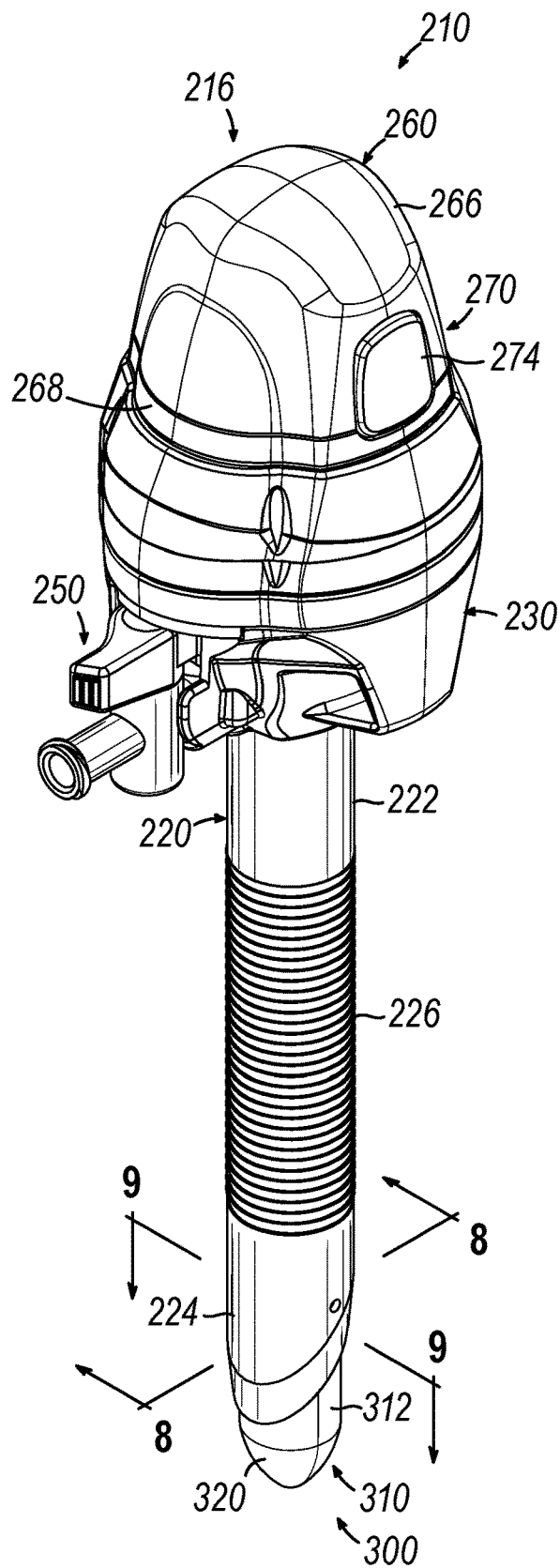
FIG. 6C depicts a perspective view of the trocar of FIG. 6A, where the cannula assembly and the obturator assembly are in an assembled state.

FIGS. 6A-6C show an alternative trocar (210) that may be used in replacement of trocar (10, 110) described above. Trocar (210) includes a cannula assembly (212) defining a working channel (214) and an obturator (216) configured to be removably inserted coaxially into working channel (214) so that the assembled trocar (210) may be directed distally through the abdominal wall (2) of the patient and into the abdominal cavity (1) in accordance with the description herein.

As will be described in greater detail below, obturator (216) includes a replaceable tip assembly (300) having a reusable portion (302) and a replaceable obturator tip (310). As will also be described in greater detail below, replaceable obturator tip (310) may be selectively replaced with a new obturator tip (310) to ensure proper tip geometry for atraumatic, yet easy-to-use, tissue spreading in accordance with the teachings herein. Therefore, reusable portion (302) and remaining portions of obturator (216) may be sterilized and reused for multiple surgical procedures, while a new obturator tip (310) may be readily incorporated to ensure proper tip geometry.

Cannula assembly (212) may be substantially similar to either cannula assembly (12, 112) described above. Cannula assembly (212) includes a cannula (220) and a seal housing (230) which together define working channel (214). Cannula (220) and seal housing (230) may be substantially similar to either (A) cannula (20) and seal housing (30), respectively, or (B) cannula (120) and seal assembly (130), respectively. In other words, cannula (220) may be configured for either single-use or multi-use purposes; while seal assembly (230) may be constructed as being partially attached to cannula (220) or as a replaceable unit.

Cannula (220) includes an elongate central tube (222), an angled cannula tip (224), and a plurality of annular ribs (226); which may be similar to elongate central tube (22, 124), angled cannula tip (24, 126), and annular rubs (26, 128) described above, respectively.

Seal housing (230) houses a pair of seal structures defining a seal assembly configured to maintain insufflation of the patient's abdominal cavity while permitting passage of surgical instruments and tissue fragments along working channel (214). Additionally, cannula assembly (212) includes an insufflation port (250), which may be substantially similar to insufflation port (50, 140) described above. Therefore, insufflation port (250) is configured to direct insufflation fluid, such as carbon dioxide, from a fluid source (not shown) distally through working channel (214) and into the patient's abdominal cavity to thereby expand (or "insufflate") the cavity with the fluid. This expansion of the abdominal cavity creates additional space for performing a laparoscopic surgical procedure with improved ease.

As shown in FIGS. 6A-6B, obturator (216) of trocar (210) includes a proximal head (260) and an elongate cylindrical shaft (262) extending distally from head (260); which are substantially similar to proximal head (60) and elongate cylindrical shaft (262) described above, with differences elaborated below. Additionally, obturator (216) includes replaceable tip assembly (300) located at a distal end of the elongate cylindrical shaft (262).

Obturator head (260) includes a domed upper body (266), a base plate (268), and an actuatable latch member (270), which includes a pair of latch arms (272) and a corresponding pair of latch buttons (274). Latch arms (272) are configured to be captured within respective slots (238) formed in a top surface of seal housing (230) to couple obturator (216) with cannula assembly (212). Latch buttons (274) are actuatable to release latch arms (272) from the slots and thereby permit separation of obturator (216) from cannula assembly (212). While not shown, obturator (216) may also include a central passage (not shown), similar to central passage (76) described above, that extends longitudinally through obturator head (260) and obturator shaft (262), and is configured to receive an endoscope (not shown) therein to provide visualization during insertion of trocar (210) through the abdominal wall of a patient. In such instances, a clamp lever (not shown) of obturator head (260) may be pivotable to selectively fix the endoscope within central passage (not shown). Of course, central passage (not shown) and clamp lever (not shown) are merely optional features and may be omitted from obturator (216) in other versions.

As mentioned above, and as best shown in FIGS. 7A-9, replaceable tip assembly (300) includes a reusable portion (302) and a replaceable obturator tip (310). As also mentioned above, and as will be described in greater detail below, replaceable obturator tip (310) may be selectively coupled and decoupled from the reusable portion (302) in order to replace a used obturator tip (310) for a new obturator tip (310).

Reusable portion (302) is fixed at the distal end of elongate cylindrical shaft (262). Reusable portion (302) includes a key post (304) and a pair of lateral snap-fit ribs (305) extending laterally from respective sides of key post (304). Key post (304) further includes a proximal narrow portion (306) extending into a distal wide portion (308). As will be described in greater detail below, key post (304) and lateral snap-fit ribs (305) are configured to selectively couple replaceable obturator tip (310) with elongate cylindrical shaft (262).

Reusable portion (302) is configured to be sterilized and reused for multiple surgical procedures. Reusable portion (302) may be formed from any suitable material as would be apparent to one skilled in the art in view of the teachings herein, such as surgical steel. In some examples, reusable portion (302) may be formed from the same material as elongate cylindrical shaft (262). Alternatively, reusable portion (302) may be formed from another suitable material that is different than the material used to form elongate cylindrical shaft (262).

Replaceable obturator tip (310) includes a coupling body (312) and a tapered distal tip (320) fixed to coupling body (312). Tapered distal tip (320) contains a suitable tip geometry that is sharp enough, yet not too sharp, in order to allow for atraumatic, yet each-to-use, tissue spreading of the patients abdominal wall (2) when replaceable tip assembly (300) is suitably assembled in accordance with the description herein. Tapered distal tip (320) may be configured for a single use (or a predetermined number of multiple uses) such that after a surgical procedure, obturator tip (310) is removed, reusable portion (302) and the rest of obturator (216) is sterilized, and a new obturator tip (310) is coupled to reusable portion (302) in accordance with the description herein. Therefore, undesirable deviation of tip geometry may be prevented from numerous uses in accordance with the description herein. Replaceable obturator tip (310) may be formed from any suitable material as would be apparent to one skilled in the art in view of the teachings herein. For instance, replaceable obturator tip (310) may be formed from any suitable plastic, any suitable metal, any suitable alloy, etc.

Coupling body (312) includes a plurality of internal ribs (316) and a plurality of gripping features (318). Gripping features (318) extend from an outer surface of coupling body (312). Gripping features (318) may help the operator suitably grasp coupling body (312) in order to couple and decouple replaceable obturator tip (310) with reusable portion (302) in accordance with the description herein. While in the current example, gripping features (318) include a plurality of longitudinally extending protrusions, any other suitable gripping feature and/or geometry may be used as would be apparent to one skilled in the art in view of the teachings herein.

Figure 9:
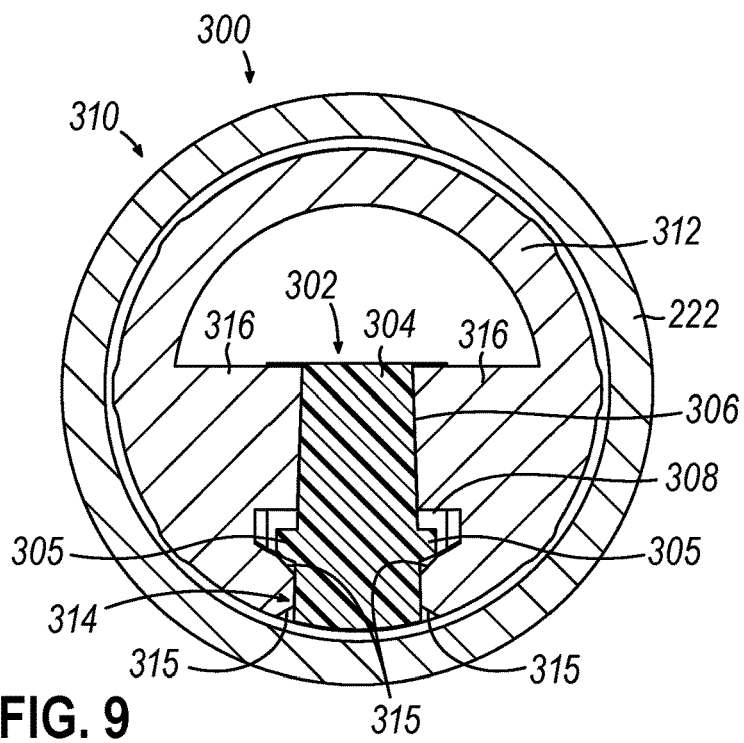
FIG. 9 depicts a cross-sectional view of the trocar of FIG. 6A, taken along line 9-9 of FIG. 6C.

The outer surface of coupling body (312) and internal ribs (316) define a complementary keyhole (314). Additionally, as best seen in FIGS. 7A and 9, the outer surface of coupling body (312) defining complementary keyhole (314) includes a pair of outwardly facing snap-fit surfaces (315) and a pair of inwardly facing snap-fit surfaces (315).

Figure 7A:
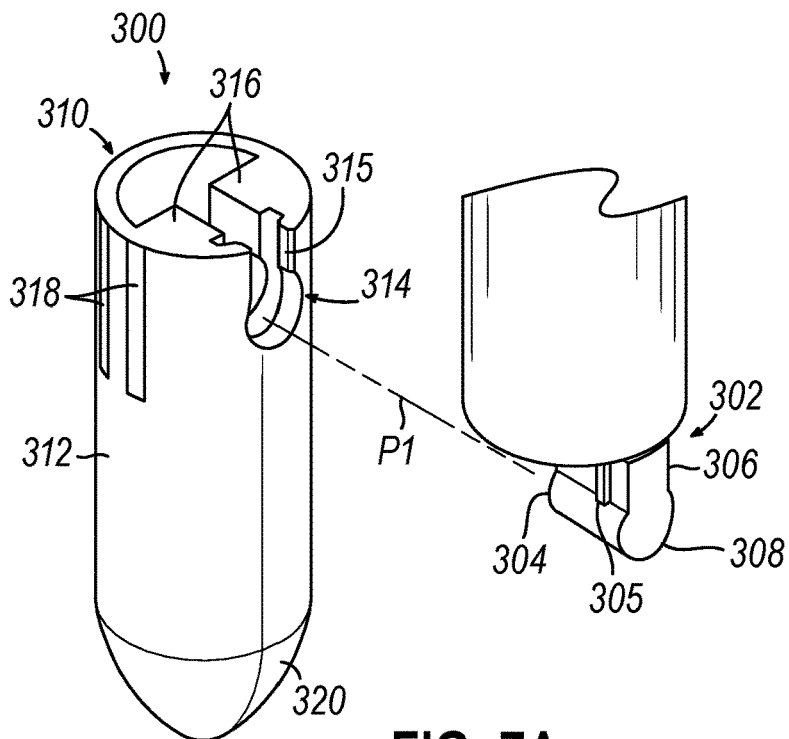
FIG. 7A depicts an enlarged perspective view of the replaceable tip assembly of FIG. 6A, where the replaceable tip assembly is in the disassembled state.
Figure 7B:
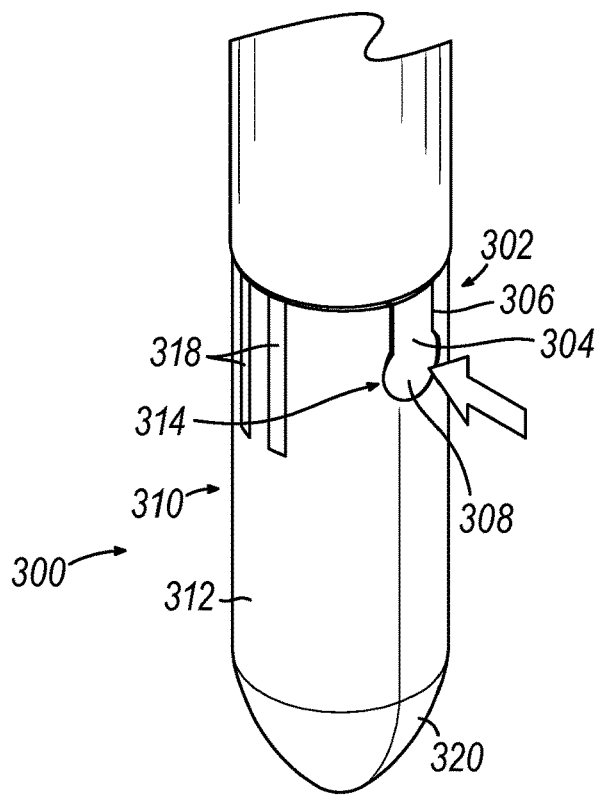
FIG. 7B depicts an enlarged perspective view of the replaceable tip assembly of FIG. 6A, where the replaceable tip assembly is in the assembled state.

As best shown in FIGS. 6A and 7A, complementary keyhole (314) is dimensioned to receive key post (304) along an insertion path (P1). In particular, as shown between FIGS. 6A-6B and 7A-7B, when complementary keyhole (314) and key post (304) are suitably aligned, the operator may advance replaceable obturator tip (310) and/or key post (304) toward each other along insertion path (P1) such that key post (304) is suitably contained within keyhole (314). While in the current example, insertion path (P1) is perpendicular (or "lateral") relative to the longitudinal central axis of trocar (210), this is merely optional. In some instances, key post (304) and keyhole (314) may be configured to be coupled along an insertion path that is oblique to the central axis of trocar (210). In other words, insertion path (P1) may extend along an axis that merely transverses, or extends across, the central axis of trocar (210) from the perspective of a two-dimensional plane containing both central axis and the axis which insertion path (P1) extends along.

Additionally, lateral snap-fit ribs (305) are dimensioned to interact with the pair of outwardly facing snap-fit surface (315) of coupling body (312) such that when key post (304) is inserted into complementary keyhole (314), ribs (305) abut against outwardly facing snap-fit surface (315) to provide a snap-fit coupling. The portion of external surface forming snap-fit surfaces (315) and/or ribs (305) may be sufficiently resilient to slightly deform as key post (304) enters keyhole (314). As best shown in FIG. 9, once key post (304) is fully inserted into complementary keyhole (314), the portion of external surface forming snap-fit surfaces (315) and/or ribs (305) resiliently return to a non-deformed position such that ribs (305) may be housed within keyhole (314) adjacent to inwardly facing snap-fit surfaces (315). Snap-fit ribs (305) and surfaces (315) may provide tactile feedback to the operator to confirm suitable coupling of reusable portion (302) with replaceable obturator tip (310).

As best shown between FIGS. 6B-6C, with replaceable obturator tip (310) suitably coupled with reusable portion (302) and the rest of obturator (216), the operator may suitably insert obturator (216) into working channel (214) of cannula assembly (212). Obturator shaft (262) is configured to be received within working channel (214) of cannula assembly (212) such that tapered distal tip (320) of replaceable obturator tip (312) extends through and distally of cannula tip (224). With trocar (210) fully assembled, the operator may use trocar (210) in accordance with the teachings herein.

Figure 8:
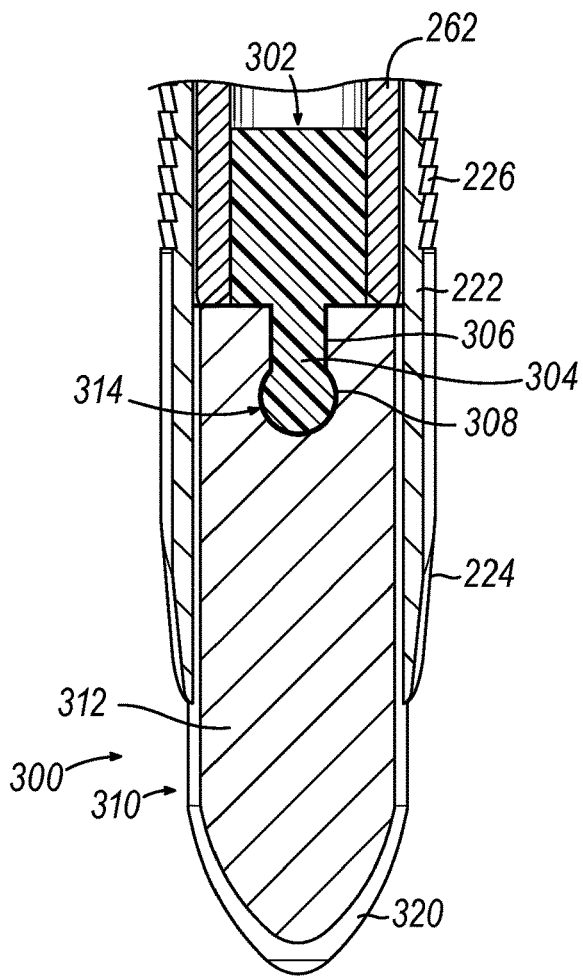
FIG. 8 depicts an enlarged cross-sectional view of the trocar of FIG. 6A, showing a distal end of the trocar, taken along line 8-8 of FIG. 6C.

As best shown in FIGS. 8-9, when key post (304) of reusable portion (302) is suitably inserted into keyhole (314) of replaceable obturator tip (310), the complementary geometry of key post (304) and keyhole (314) are configured to prevent movement of obturator tip (310) relative to reusable portion (302) in all directions that are not parallel along insertion path (P1). For instance, the connection between replaceable obturator tip (310) and obturator shaft (262) as described above effectively resists motion of obturator tip (310) relative to obturator shaft (262) in an axial direction along the longitudinal axis of obturator shaft (262), in response to axial forces. This connection also effectively resists rotational motion of obturator tip (310) relative to obturator shaft (262) about the longitudinal axis in response to torsional forces; for example, when obturator tip (310) is being advanced distally through the abdominal wall (2) of a patient in the manner described above in connection with FIGS. 3A-3B.

As best shown in FIG. 9, snap-fit ribs (305) and inwardly facing snap-fit surface (315) may abut against each other in order to prevent key post (304) from inadvertently exiting out of keyhole (314) along insertion path (P1).

Side walls of narrow portion (306) that contact internal ribs (316) may have a slight taper such that the end of narrow portion (306) adjacent to the outer surface of coupling body (312) is wider than the end of narrow portion (306) housed within keyhole (314). The slight taper of narrow portion (306) may allow the side walls of narrow portion (306) to abut against internal ribs (316) when key post (304) is suitably inserted into keyhole (314), thereby preventing accidental over-insertion of key post (304) into keyhole (314).

Additionally, when trocar (210) is assembled, key post (304) and keyhole (314) are both suitably contained within working channel (214) of cannula (220) such that the interior wall of cannula (220) may also help to keep replaceable obturator tip (310) aligned with reusable portion (302). In other words, when trocar (210) is suitably assembled for use in accordance with the description herein, the interior wall of cannula (220) may help prevent (A) key post (304) from exiting out of keyhole (314) along insertion path (P1), and (B) over insertion of key post (304) into keyhole (314). Therefore, in some instances, snap-fit surfaces (315) and snap-fit ribs (305) may be omitted. Also, in some instances, the slight taper of narrow portion (306) to prevent accidental over-insertion may also be omitted.

After use of obturator (216) in accordance with the description herein, the operator may remove replaceable obturator tip (310) from reusable portion (302) by actuating key post (304) out of keyhole (314) along insertion path (P1) with sufficient force to overcome the snap-fit coupling between snap-fit ribs (305) and inwardly facing snap-fit surfaces (315). The operator may then discard the used replaceable obturator tip (310), sterilize the rest of obturator (216), and couple a new obturator tip (310) to the sterilized reusable portion (302) in preparation for another surgical procedure.

In the current example, proximal narrow portion (306) includes a rectangular cross-sectional geometry while distal wide portion (308) includes a circular cross-sectional geometry. However, it should be understood that key post (304) may have any suitable geometry as would be apparent to one skilled in the art in view of the teachings herein. For example, key post (304) may include a dove-tail geometry that widens as key post (304) extends distally from elongate cylindrical shaft (262). As another example, key post (304) may include an undulating surface.

In the current example, reusable portion (302) includes the male coupling portion (i.e. key post (304)), while replaceable obturator tip (310) includes the female coupling portion (i.e. the keyhole (314)). However, this is merely optional, as the reusable portion (302) may include the female coupling portion and the replaceable obturator tip (310) may include the male coupling portion.

Figure 10A:
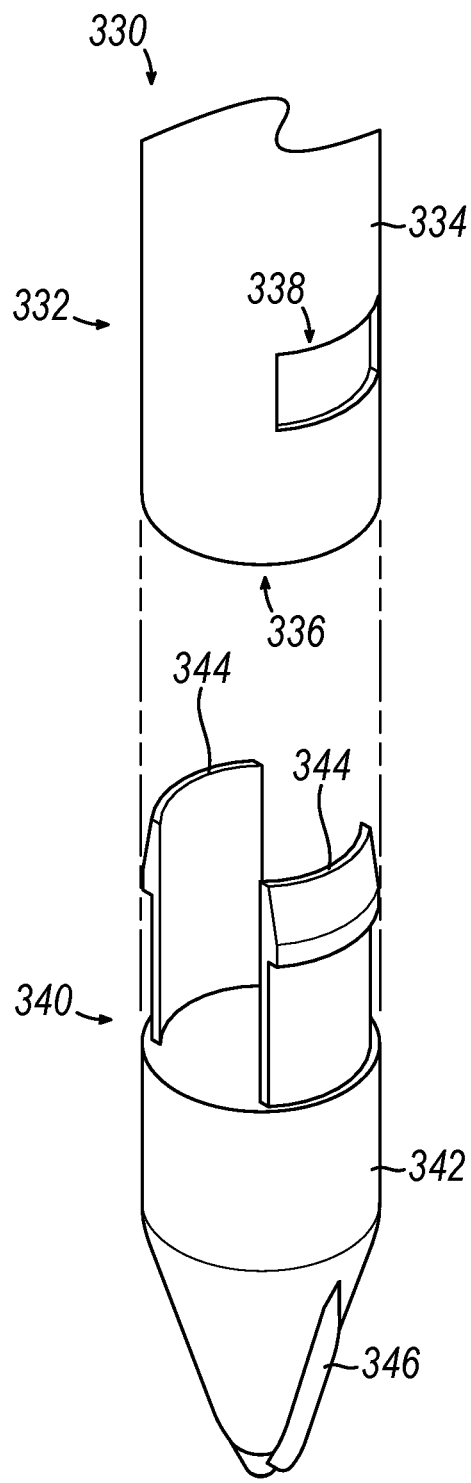
FIG. 10A depicts an enlarged perspective view of an alternative replaceable tip assembly, where the replaceable tip assembly is in a disassembled state.
Figure 10B:
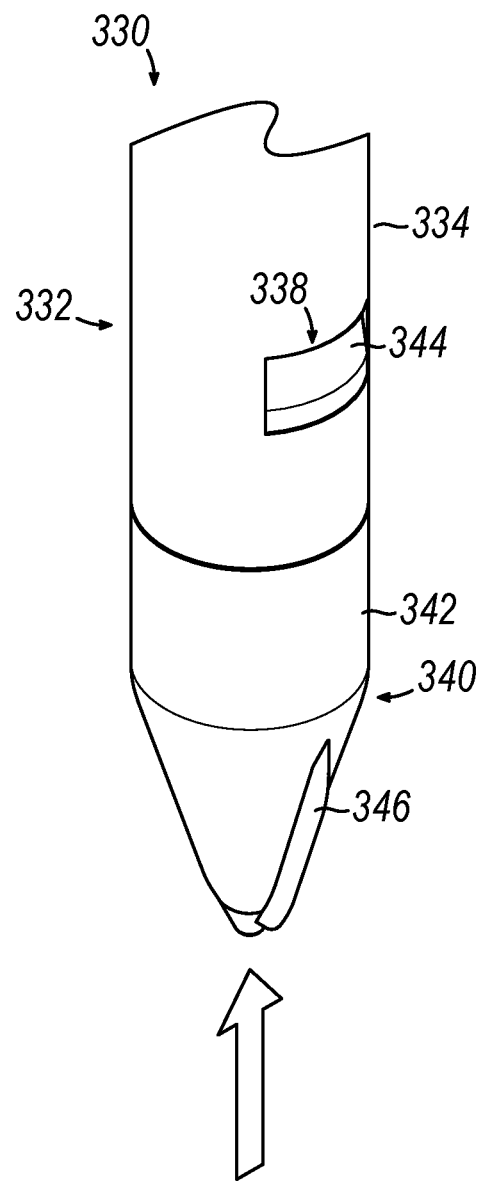
FIG. 10B depicts an enlarged perspective view of the replaceable tip assembly of FIG. 10A, where the replaceable tip assembly is in an assembled state.

FIGS. 10A-10B show another exemplary replaceable tip assembly (330) that may be readily incorporated into obturator (216) in replacement of replaceable tip assembly (300) described above. Replaceable tip assembly (330) includes a reusable portion (332) and a replaceable obturator tip (340). As will be described in greater detail below, replaceable obturator tip (340) may be selectively coupled and decoupled from the reusable portion (332) in order to replace a used obturator tip (340) for a new obturator tip (340).

Reusable portion (332) may be fixed at the distal end of elongate cylindrical shaft (262). Reusable portion (332) includes a cylindrical body that defines an internal passage extending between an open distal end (336) and a pair of lateral cutouts (338).

Similar to reusable portion (302) described above, reusable portion (332) is configured to be sterilized and reused for multiple surgical procedures. Reusable portion (332) may be formed from any suitable material as would be apparent to one skilled in the art in view of the teachings herein, such as surgical steel. In some examples, reusable portion (332) may be formed from the same material as elongate cylindrical shaft (262). Alternatively, reusable portion (332) may be formed from another suitable material that is different than the material used to form elongate cylindrical shaft (262).

Replaceable obturator tip (340) includes a coupling body (342) and a tapered distal tip (346) fixed to coupling body (342). Tapered distal tip (346) contains a suitable tip geometry that is sharp enough, yet not too sharp, in order to allow for atraumatic, yet each-to-use, tissue spreading of the patients abdominal wall (2) when replaceable tip assembly (330) is suitably assembled in accordance with the description herein. Tapered distal tip (346) may be configured for a single use (or a predetermined number of multiple uses) such that after a surgical procedure, obturator tip (340) is removed, reusable portion (332) and the rest of obturator (216) is sterilized, and a new obturator tip (340) is coupled to reusable portion (332) in accordance with the description herein. Therefore, undesirable deviation of tip geometry may be prevented from numerous uses in accordance with the description herein.

Coupling body (342) includes a pair of proximally extending resilient latches (344). As best seen between FIGS. 10A-10B, resilient latches (344) are configured to flex inwardly while being inserted into open distal end (336) due to contact between resilient latches (344) and the interior surface of the cylindrical body of reusable portion (332). Once a proximal end of resilient latches (344) is suitably aligned with lateral cutouts (338), resilient latches (344) may flex laterally outwardly due to no longer being in suitable contact with the interior surface of reusable portion (332). Once in the position shown in FIG. 10B, a distally presented shoulder of each resilient latch (344) may abut against a portion of a respective lateral cutout (338), therefore preventing replaceable obturator tip (340) from disassociating with reusable portion (332). In other words, resilient latches (344) and lateral cutouts (338) may fix obturator tip (340) to reusable portion (332).

Additionally, a proximal facing shoulder of coupling body (342) may abut against the distal end of reusable portion (332) defining open distal end (336), thereby preventing replaceable tip (340) from translating proximally past the position shown in FIG. 10B.

With replaceable obturator tip (340) suitably coupled with reusable portion (332) and the rest of obturator (216), the operator may suitably insert obturator (216) into working channel (214) of cannula assembly (212) such that the operator may use trocar (210) in accordance with the teachings herein.

After use of obturator (216) in accordance with the description herein, the operator may remove replaceable obturator tip (340) from reusable portion (332) by actuating both resilient latches (334) inwardly such that distally facing shoulders of resilient latches (334) no longer abut against reusable portion (332) defining lateral cutouts (338). Any suitable tool may be used to actuate resilient latches (334) inwardly as would be apparent to one skilled in the art in view of the teachings herein. Simultaneously, the operator may distally pull on replaceable tip (340) such that resilient latches (334) engage the interior surface of reusable portion (332). The operator may further pull replaceable tip (340) out of reusable portion (332), discard the used replaceable obturator tip (340), sterilize the rest of obturator (216) and reusable portion (332), and couple a new obturator tip (340) to the sterilized reusable portion (332) in preparation for another surgical procedure.

Figure 11A:
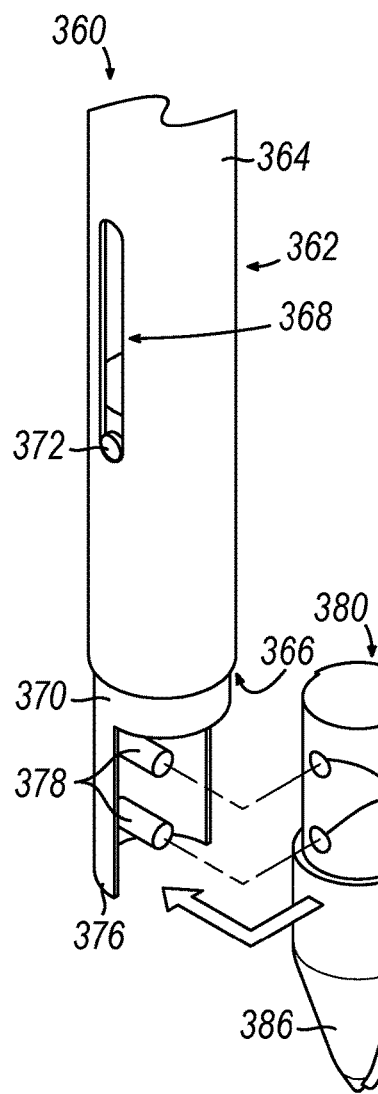
FIG. 11A depicts an enlarged perspective view of a replaceable tip assembly having a replaceable obturator tip and a reusable portion, where the reusable portion further includes a tubular body and a sliding drawer, where the replaceable obturator tip is disassembled from the sliding drawer, where the sliding drawer is in an extended position.
Figure 11B:
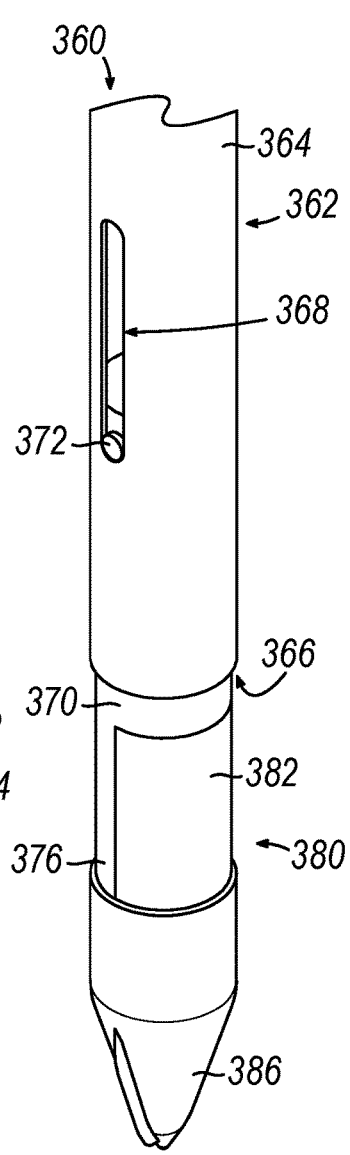
FIG. 11B depicts an enlarged perspective view of the replaceable tip assembly of FIG. 11A, where the replaceable obturator tip is assembled with the sliding drawer, where the sliding drawer is in the extended position.
Figure 11C:
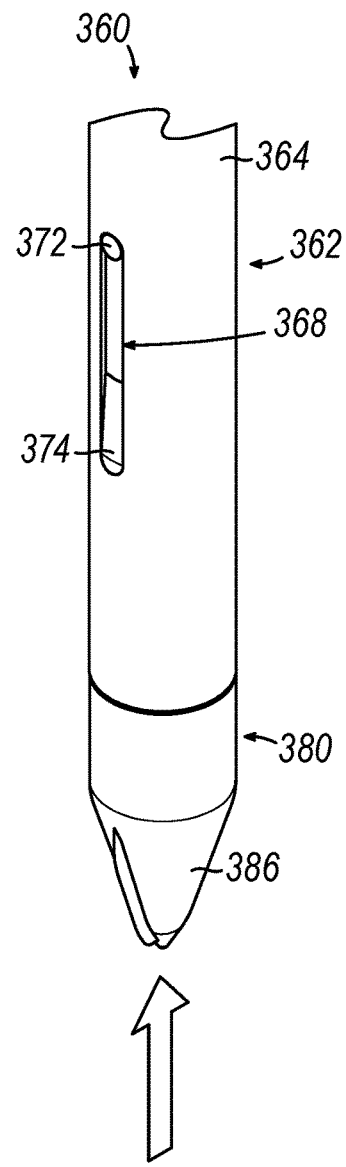
FIG. 11C depicts an enlarged perspective view of the replaceable tip assembly of FIG. 11A, where the replaceable obturator tip is assembled with the sliding drawer, where the sliding drawer is in a retracted position.

FIGS. 11A-11C show another exemplary replaceable tip assembly (360) that may be readily incorporated into obturator (216) in replacement of replaceable tip assembly (300) described above. Replaceable tip assembly (360) includes a reusable portion (362) and a replaceable obturator tip (380). As will be described in greater detail below, replaceable obturator tip (380) may be selectively coupled and decoupled from the reusable portion (362) in order to replace a used obturator tip (380) for a new obturator tip (380).

Figure 12:
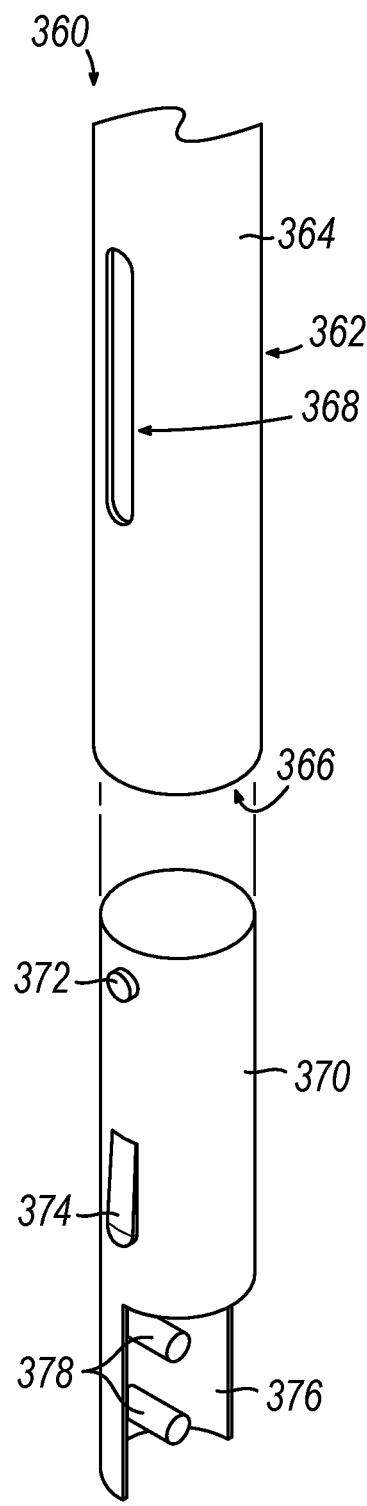
FIG. 12 depicts an enlarged exploded view of the reusable portion of the replaceable tip assembly of FIG. 11A.

Reusable portion (332) includes a tubular body (364) and a sliding drawer (370) slidably attached to tubular body (364) between an extended position (as shown in FIGS. 11A-11B) and a retracted position (as shown in FIG. 11C). Tubular body (364) may be fixed at the distal end of elongate cylindrical shaft (262). Tubular body (364) defines an internal passage extending between an open distal end (366) and an elongate slot (338). As best seen in FIG. 12, sliding drawer (370) includes a cylindrical body dimensioned to slidably fit within internal passage defined by tubular body (364).

Sliding drawer (370) also includes a transverse pin (372) and a resilient latch (374) disposed on the outer surface of cylindrical body. Transverse pin (372) is slidably contained within elongate slot (338) such that elongate slot (338) defines the range of travel which sliding drawer (370) may translate. Therefore, transverse pin (372) and elongate slot (338) together prevent sliding drawer (370) from disassociating with tubular body (364).

Resilient latch (374) is configured to selectively lock sliding drawer (370) in the retracted position. Resilient latch (374) may compress due to contact with the inner wall of tubular body (364) when sliding drawer (370) is distal compared to the retracted position. Once sliding drawer (370) is actuated into the retracted position, resilient latch (374) may expand within elongate slot (368) such that sliding drawer (370) is prevented from sliding distally relative to tubular body (364). Additionally, when sliding drawer (370) is in the retracted position, transverse pin (372) abuts against the proximal end of elongate slot (338) such that sliding drawer (370) is prevented from translating proximally within tubular body (364). In order to unlock sliding drawer (370) from the retracted position, the operator may drive resilient latch (374) toward cylindrical body of sliding drawer (370) such that resilient latch (374) no longer abuts against the distal end of elongate slot (338). Simultaneously, the operator may pull sliding drawer (370) distally out of the retracted position to unlock sliding drawer (370).

Sliding drawer (370) also includes a distal sheath (376) and a pair of coupling pins (378). Distal sheath (376) is dimensioned to receive a proximal coupling body (382) of replaceable tip (380). Coupling pins (378) are dimensioned to be inserted into pin holes (384) defined by proximal coupling body (382) of replaceable tip (380).

Similar to reusable portion (302) described above, reusable portion (362) is configured to be sterilized and reused for multiple surgical procedures. Reusable portion (362) may be formed from any suitable material as would be apparent to one skilled in the art in view of the teachings herein, such as surgical steel. In some examples, reusable portion (362) may be formed from the same material as elongate cylindrical shaft (262). Alternatively, reusable portion (362) may be formed from another suitable material that is different than the material used to form elongate cylindrical shaft (262).

Replaceable obturator tip (380) includes a coupling body (382) and a tapered distal tip (386) fixed to coupling body (382). Tapered distal tip (386) contains a suitable tip geometry that is sharp enough, yet not too sharp, in order to allow for atraumatic, yet each-to-use, tissue spreading of the patients abdominal wall (2) when replaceable tip assembly (380) is suitably assembled in accordance with the description herein. Tapered distal tip (386) may be configured for a single use (or a predetermined number of multiple uses) such that after a surgical procedure, obturator tip (380) is removed, reusable portion (362) and the rest of obturator (216) is sterilized, and a new obturator tip (380) is coupled to reusable portion (362) in accordance with the description herein. Therefore, undesirable deviation of tip geometry may be prevented from numerous uses in accordance with the description herein.

As mentioned above, coupling body (342) defines a pair of pin holes (384). As best seen between FIGS. 11A-11B, coupling body (342) may be inserted within sheath (376) of sliding drawer (370), while sliding drawer (370) is in the extended position, such that pins (378) are inserted into pin holes (384). At this moment, as shown in FIG. 11B, coupling body (342) is longitudinally constrained with sliding drawer (370). Next, as shown between FIGS. 11B-11C, the operator may proximally advance sliding drawer (370), while coupling body (342) is attached, from the extended position to the locked, retracted position. Therefore, sliding drawer (370), as well as obturator tip (380), becomes locked relative to tubular body (364) in accordance with the description above. Additionally, proximal coupling body (382) of obturator tip (380) and sheath (376) of sliding drawer (370) become housed within tubular body (364), therefore laterally constraining obturator tip (380) relative to tubular body (364).

With replaceable obturator tip (380) suitably coupled with reusable portion (362) and the rest of obturator (216), the operator may suitably insert obturator (216) into working channel (214) of cannula assembly (212) such that the operator may use trocar (210) in accordance with the teachings herein.

After use of obturator (216) in accordance with the description herein, the operator may remove replaceable obturator tip (380) from reusable portion (332) by actuating resilient latch (374) inwardly such that resilient latch (374) no longer abuts against the distal end of elongate slot (368). Any suitable tool may be used to actuate resilient latch (374) inwardly as would be apparent to one skilled in the art in view of the teachings herein. Simultaneously, the operator may distally pull on replaceable tip (340) such that sliding drawer (370) moves distally from the retracted position into the extended position. The operator may further pull replaceable tip (380) out of reusable portion (362), discard the used replaceable obturator tip (380), sterilize the rest of obturator (216) and reusable portion (362), and couple a new obturator tip (380) to the sterilized reusable portion (362) in preparation for another surgical procedure.

It should be understood that while replaceable obturator tips (310, 340, 380) are described above as being used once and disposed of, in some instances, obturator tips (310, 340, 380) may be sterilized and reused multiple times, then replaced after a certain number of uses. In such instances, the remaining portions of obturator (216) may be sterilized and reused many more times compared to a single replaceable obturator tip (310, 340, 380).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device comprising: (a) an obturator head; (b) an elongated shaft extending distally from the obturator head along a longitudinal axis, wherein the elongated shaft is dimensioned to fit within a working channel of a cannula; and (c) an obturator tip assembly, comprising: (i) a reusable portion attached to a distal portion of the elongated shaft, wherein the reusable portion is configured to be sterilized with the elongated shaft, and (ii) a replaceable tip, comprising: (A) a tapered distal tip configured to facilitate insertion of the surgical access device through a body wall of the patient, and (B) a proximal coupling body configured to selectively couple with the reusable portion, wherein the replaceable tip, in its entirety, is movable relative to the reusable portion along a mating path in order to couple the proximal coupling body with the reusable portion, wherein the mating path extends laterally relative to the longitudinal axis.

Example 2

The surgical access device of Example 1, wherein the reusable portion comprises a male coupling portion, wherein the proximal coupling body comprise a complementary female coupling portion configured to receive the male coupling portion.

Example 3

The surgical access device of Example 2, wherein the male coupling portion comprises a key post, wherein the female coupling portion comprise a keyhole.

Example 4

The surgical access device of Example 2, wherein the male coupling portion comprises a dovetail, wherein the female coupling portion comprises a dovetail slot.

Example 5

The surgical access device of any one or more of Examples 2 through 4, wherein the male coupling portion further comprises a snap-fit rib, wherein the female coupling portion is at least partially defined by a snap-fit surface configured to abut against the snap-fit rib as the proximal coupling body couples with the reusable portion.

Example 6

The surgical access device of any one or more of Examples 2 through 5, wherein the proximal coupling body further comprises a plurality of internal ribs defining the complementary female coupling portion.

Example 7

The surgical access device of Example 6, wherein the plurality of internal ribs is configured to abut against the male coupling portion of the reusable portion in order to prevent over insertion of the male coupling portion into the female coupling portion.

Example 8

The surgical access device of any one or more of Examples 1 through 8, wherein the proximal coupling body further comprises a user gripping feature.

Example 9

The surgical access device of any one or more of Examples 1 through 8, wherein the replaceable tip is formed from a plastic material.

Example 10

The surgical access device of any one or more of Examples 1 through 9, wherein the replaceable tip is configured to couple with the reusable portion via a snap-fitting.

Example 11

The surgical access device of any one or more of Examples 1 through 10, further comprising a cannula assembly.

Example 12

The surgical access device of Example 11, wherein the cannula assembly further comprises the cannula defining the working channel, wherein the working channel is configured to receive a surgical instrument therethrough to access a surgical site within a body cavity of a patient when the elongated shaft is removed from the working channel.

Example 13

The surgical access device of Example 12, wherein the cannula assembly further comprises a seal assembly defining a portion of the working channel.

Example 14

The surgical access device of Example 13, wherein the seal assembly is releasably coupled with the cannula.

Example 15

The surgical access device of any one or more of Examples 1 through 14, wherein the obturator head comprises a dome shaped body.

Example 16

A surgical access device comprising: (a) a cannula assembly including: (i) a cannula, (ii) a seal assembly coupled with a proximal end of the cannula, and (iii) a working channel at least partially defined by the cannula and the seal assembly extending longitudinally along a central axis of the cannula assembly, wherein the working channel is configured to receive a surgical instrument therethrough to access to a surgical site within a body cavity of a patient; and (b) an obturator, wherein the obturator is configured to removably couple with the cannula assembly along the central axis to facilitate insertion of the surgical access device through a body wall of the patient, wherein the obturator comprises: (i) an elongated shaft extending distally from the obturator head along a longitudinal axis, wherein the elongated shaft is dimensioned to fit within the working channel of the cannula assembly; and (ii) a replaceable tip, comprising: (A) a tapered distal tip, and (B) a proximal coupling body configured to selectively couple with the elongated shaft, wherein the replaceable tipis movable relative to the elongated shaft along a coupling path that is non-parallel relative to the central axis.

Example 17

The surgical access device of Example 16, wherein one of the elongated shaft or the proximal coupling body comprises a key post, wherein the other of the elongated shaft or the proximal coupling body defines a complementary keyhole configured to receive the key post.

Example 18

The surgical access device of Example 17, wherein the cannula is configured to house the key post and the keyhole while the obturator is coupled with the cannula assembly.

Example 19

The surgical access device of any one or more of Examples 16 through 18, wherein the cannula comprises a plurality of annular ribs.

Example 20

A surgical access device comprising: (a) an obturator head; (b) an elongated shaft extending distally from the obturator head along a longitudinal axis; and (c) an obturator tip assembly, comprising: (i) a reusable portion attached to a distal portion of the elongated shaft, wherein the reusable portion comprises a first mating feature, wherein the reusable portion is configured to be sterilized with the elongated shaft, and (ii) a replaceable tip, comprising: (A) a distal tip configured to facilitate insertion of the surgical device through a body wall of the patient, and (B) a proximal coupling body fixed to the distal tip, wherein the proximal coupling body comprises a second mating feature, wherein the second mating feature is movable relative to the first mating feature of the reusable portion along a mating path that is transverse relative to the longitudinal axis.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/0338273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, issued as U.S. Pat. No.

11,712,267 on Aug. 1, 2023; U.S. patent application Ser. No. 17/213,434, entitled "Latchless Obturator with Interference Fit Feature," filed on Mar. 26, 2021, published as U.S. Pub. No. 2021/0338269 on Nov. 4, 2021; U.S. patent application Ser. No. 17/213,437, entitled "Balancing Feature for Reusable Trocar," filed on Mar. 26, 2021, issued as U.S. Pat. No. 11,559,329 on Jan. 24, 2023; U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical access device comprising:
   (a) an obturator head;
   (b) an elongated shaft extending distally from the obturator head along a longitudinal axis, wherein the elongated shaft is dimensioned to fit within a working channel of a cannula; and
   (c) an obturator tip assembly, comprising:
      (i) a reusable portion attached to a distal portion of the elongated shaft, wherein the reusable portion is configured to be sterilized with the elongated shaft, wherein the reusable portion comprises a male coupling portion extending distally from the elongated shaft, and
      (ii) a replaceable tip, comprising:
         (A) a tapered distal tip configured to facilitate insertion of the surgical access device through a body wall of a patient, and
         (B) a proximal coupling body configured to selectively couple with the reusable portion, wherein the proximal coupling body defines a female coupling portion having a tapered surface that at least partially defines a laterally presented opening dimensioned to receive the male coupling portion,
      wherein the replaceable tip, in its entirety, is movable relative to the reusable portion along a mating path in order to couple the proximal coupling body with the reusable portion, wherein the mating path extends laterally relative to the longitudinal axis, wherein the tapered surface is configured to directly engage the male coupling portion to inhibit over insertion of the replaceable tip along the mating path.

2. The surgical access device of claim 1, wherein the male coupling portion comprises a key post, wherein the female coupling portion comprise a keyhole.

3. The surgical access device of claim 1, wherein the male coupling portion comprises a dovetail, wherein the female coupling portion comprises a dovetail slot.

4. The surgical access device of claim 1, wherein the male coupling portion further comprises a snap-fit rib, wherein the female coupling portion is at least partially defined by a snap-fit surface configured to abut against the snap-fit rib as the proximal coupling body couples with the reusable portion.

5. The surgical access device of claim 1, wherein the proximal coupling body further comprises a plurality of internal ribs defining the complementary female coupling portion.

6. The surgical access device of claim 5, wherein the plurality of internal ribs is configured to abut against the male coupling portion of the reusable portion in order to prevent over insertion of the male coupling portion into the female coupling portion.

7. The surgical access device of claim 1, wherein the proximal coupling body further comprises a user gripping feature.

8. The surgical access device of claim 1, wherein the replaceable tip is formed from a plastic material.

9. The surgical access device of claim 1, wherein the replaceable tip is configured to couple with the reusable portion via a snap-fitting.

10. The surgical access device of claim 1, further comprising a cannula assembly.

11. The surgical access device of claim 10, wherein the cannula assembly further comprises the cannula defining the working channel, wherein the working channel is configured to receive a surgical instrument therethrough to access a surgical site within a body cavity of a patient when the elongated shaft is removed from the working channel.

12. The surgical access device of claim 11, wherein the cannula assembly further comprises a seal assembly defining a portion of the working channel.

13. The surgical access device of claim 12, wherein the seal assembly is releasably coupled with the cannula.

14. The surgical access device of claim 1, wherein the obturator head comprises a dome shaped body.

15. A surgical access device comprising:
(a) a cannula assembly including:
 (i) a cannula,
 (ii) a seal assembly coupled with a proximal end of the cannula, and
 (iii) a working channel at least partially defined by the cannula and the seal assembly extending longitudinally along a central axis of the cannula assembly, wherein the working channel is configured to receive a surgical instrument therethrough to access to a surgical site within a body cavity of a patient; and
(b) an obturator, wherein the obturator is configured to removably couple with the cannula assembly along the central axis to facilitate insertion of the surgical access device through a body wall of the patient, wherein the obturator comprises:
 (i) an elongated shaft extending along a longitudinal axis, wherein the elongated shaft is dimensioned to fit within the working channel of the cannula assembly; and
 (ii) a replaceable tip, comprising:
  (A) a tapered distal tip, and
  (B) a proximal coupling body configured to selectively couple with the elongated shaft, wherein the replaceable tip is movable relative to the elongated shaft along a coupling path that is non-parallel relative to the central axis,
  wherein one of the elongated shaft or the proximal coupling body includes a laterally presented opening and a tapered surface that at least partially defines the laterally presented opening, and the other of the elongated shaft or the proximal coupling body includes a protrusion configured to be received by the laterally presented opening,
  wherein the tapered surface is configured to engage the protrusion and thereby inhibit over-insertion of the protrusion into a laterally presented opening.

16. The surgical access device of claim 15, wherein one of the elongated shaft or the proximal coupling body comprises a key post, wherein the other of the elongated shaft or the proximal coupling body defines a complementary keyhole configured to receive the key post.

17. The surgical access device of claim 16, wherein the cannula is configured to house the key post and the keyhole while the obturator is coupled with the cannula assembly.

18. The surgical access device of claim 15, wherein the cannula comprises a plurality of annular ribs.

19. A surgical access device comprising:
(a) an obturator head;
(b) an elongated shaft extending distally from the obturator head along a longitudinal axis; and
(c) an obturator tip assembly, comprising:
 (i) a reusable portion attached to a distal portion of the elongated shaft, wherein the reusable portion comprises a first mating feature, wherein the reusable portion is configured to be sterilized with the elongated shaft, and
 (ii) a replaceable tip, comprising:
  (A) a distal tip configured to facilitate insertion of the surgical device through a body wall of a patient, and
  (B) a proximal coupling body fixed to the distal tip, wherein the proximal coupling body comprises a second mating feature,
 wherein the first and second mating features are configured to couple along a path that extends transversely to the longitudinal axis,
 wherein the first and second mating features include respective first and second snap-fit features that extend parallel to the longitudinal axis and are configured to releasably engage one another to inhibit relative movement between the replaceable tip and the reusable portion along the path.

\* \* \* \* \*